US011135326B2

(12) United States Patent
McWhorter et al.

(10) Patent No.: US 11,135,326 B2
(45) Date of Patent: *Oct. 5, 2021

(54) STORAGE-STABLE AQUEOUS SOLUTIONS OF CHLORINE DIOXIDE AND METHODS FOR PREPARING AND USING THEM

(71) Applicant: CDG ENVIRONMENTAL, LLC, Allentown, PA (US)

(72) Inventors: Thomas Ellsworth McWhorter, Allentown, PA (US); Aaron Rosenblatt, New York, NY (US); Robert Shay, Allentown, PA (US); Barzin Keramati, Bethlehem, PA (US); Peter Kazlas, Allentown, PA (US); Madhu Anand, Allentown, PA (US); John Peter Hobbs, Lansdale, PA (US)

(73) Assignee: CDG ENVIRONMETAL, LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/419,376

(22) Filed: Jan. 30, 2017

(65) Prior Publication Data

US 2017/0136137 A1 May 18, 2017

Related U.S. Application Data

(63) Continuation-in-part of application No. 14/824,548, filed on Aug. 12, 2015, now Pat. No. 9,580,317, which is a continuation of application No. 12/296,049, filed as application No. PCT/US2006/060879 on Nov. 14, 2006, now Pat. No. 9,302,911.

(60) Provisional application No. 60/736,636, filed on Nov. 14, 2005.

(51) Int. Cl.
| | |
|---|---|
| *A61L 2/18* | (2006.01) |
| *A23L 3/358* | (2006.01) |
| *C02F 1/50* | (2006.01) |
| *A01N 59/00* | (2006.01) |
| *A61K 33/00* | (2006.01) |
| *C01B 11/02* | (2006.01) |
| *A61K 33/20* | (2006.01) |

(52) U.S. Cl.
CPC .............. *A61L 2/18* (2013.01); *A01N 59/00* (2013.01); *A23L 3/358* (2013.01); *A61K 33/00* (2013.01); *A61K 33/20* (2013.01); *C01B 11/022* (2013.01); *C01B 11/024* (2013.01); *C01B 11/028* (2013.01); *C02F 1/50* (2013.01); *A23V 2002/00* (2013.01); *C02F 2303/04* (2013.01); *Y10T 428/13* (2015.01); *Y10T 428/131* (2015.01); *Y10T 428/1334* (2015.01); *Y10T 428/1352* (2015.01)

(58) Field of Classification Search
CPC ....................................................... A61L 2/18
See application file for complete search history.

(56) References Cited

U.S. PATENT DOCUMENTS

| | | | |
|---|---|---|---|
| 2,309,457 | A | 1/1943 | Hutchinson |
| 4,430,226 | A | 2/1984 | Hegde et al. |
| 4,681,739 | A | 7/1987 | Rosenblatt et al. |
| 4,853,270 | A | 8/1989 | Wycech |
| 4,948,641 | A | 8/1990 | Shantz et al. |
| 5,006,326 | A | 4/1991 | Mayurnik et al. |
| 5,039,423 | A | 8/1991 | Kelley |
| 5,110,580 | A | 5/1992 | Rosenblatt et al. |
| 5,182,122 | A | 1/1993 | Uehara et al. |
| 5,234,678 | A | 8/1993 | Rosenblatt et al. |
| 5,770,135 | A | 6/1998 | Hobbs et al. |
| 5,855,861 | A | 1/1999 | Lee |
| 6,051,135 | A | 4/2000 | Lee et al. |
| 6,284,152 | B1 | 9/2001 | Kross |
| 2002/0037248 | A1 | 5/2002 | Bechberger et al. |
| 2003/0215381 | A1 | 11/2003 | Rosenblatt et al. |
| 2004/0022667 | A1 | 2/2004 | Lee et al. |
| 2004/0211746 | A1 | 11/2004 | Trude |
| 2005/0079230 | A1 | 4/2005 | Lee et al. |
| 2007/0098591 | A1 | 5/2007 | Frinke et al. |
| 2011/0233147 | A1 | 9/2011 | Hayafuji et al. |

FOREIGN PATENT DOCUMENTS

WO      9924356 A1    5/1999

OTHER PUBLICATIONS

Australian Office Action for Australian Patent Application No. 2006332600 dated Dec. 20, 2010.
Australian Office Action for Australian Patent Application No. 2006332600 dated May 6, 2011.
Bohner et al., Corrosivity of chlorine dioxide used as a sanitizer in ultrafiltration systems, Journal of Diary Science, 74 (10), 3348-3352, Oct. 1991.
Canadian Office Action for CA 2,629,888, dated Oct. 17, 2012.
Canadian Office Action for CA 2,675,574, dated Feb. 7, 2013.
Desai, U.J., "Comparative Analytical Methods for the Measurement of Chlorine Dioxide," Master Thesis—Environmental Engineering , Virginia Polytechnic Institute and State University, Blacksburg, VA, 2002.
Entire Patent Prosecution History of U.S. Appl. No. 12/296,051, filed Nov. 11, 2008, entitled "Use of Storage-Stable Aqueous Solutions of Chlorine Dioxide to Generate Pure Chlorine Dioxide Gas for Decontamination."

(Continued)

*Primary Examiner* — Sarah Alawadi
(74) *Attorney, Agent, or Firm* — RatnerPrestia

(57) ABSTRACT

Stable, aqueous solutions of chlorine dioxide and methods for producing stable, aqueous solutions of chlorine dioxide are disclosed. Generally, the chlorine dioxide solutions of the invention are aqueous solutions containing about 1000 ppm by weight or less of total impurities and/or 10 ppm or less of manganese and iron combined. The aqueous chlorine dioxide solutions are storage stable for at least 90 days at 25° C. and maintain at least 75% of the initial chlorine dioxide concentration. Methods of preparing, using and transporting the chlorine dioxide solutions are also disclosed.

15 Claims, 13 Drawing Sheets

(56) References Cited

OTHER PUBLICATIONS

Entire Patent Prosecution History of U.S. Appl. No. 13/365,869, filed Feb. 3, 2012, entitled "Use of Storage-Stable Aqueous Solutions of Chlorine Dioxide to Generate Pure Chlorine Dioxide Gas for Decontamination."
Entire Patent Prosecution History of U.S. Appl. No. 13/365,885, filed Feb. 3, 2012, entitled "Use of Storage-Stable Aqueous Solutions of Chlorine Dioxide to Generate Pure Chlorine Dioxide Gas for Decontamination."
Entire Patent Prosecution History of U.S. Appl. No. 13/365,902, filed Feb. 3, 2012, entitled "Use of Storage-Stable Aqueous Solutions of Chlorine Dioxide to Generate Pure Chlorine Dioxide Gas for Decontamination."
Entire Patent Prosecution History of U.S. Appl. No. 13/365,912, filed Feb. 3, 2012, entitled "Use of Storage-Stable Aqueous Solutions of Chlorine Dioxide to Generate Pure Chlorine Dioxide Gas for Decontamination."
Finch, G.R. et al., "Synergistic Effects of Multiple Disinfectants," AWWA Research Foundation and American Water Association, 2000.
Harris, C.L., "The Effects of Predisinfection with Chlorine Dioxide on the Formation of Haloacetic Acids and Thihalomethanes in a Drinking Water Supply", Masters Thesis—Environmental Engineering, Virginia Polytechnic Institute and State University, Blacksburg, VA 2001.
International Search Report dated Dec. 6, 2007 for International Application No. PCT/US2006/060879.
International Search Report dated Jul. 3, 2008 for International Application No. PCT/US2007/066081.
Li, H. et al., "Sequental Disinfection Design Criteria for Inactivation of Cryposporidium Oocysts in Drinking Water," AWWA Research Foundation and American Water Works Association, 2001.
Lindner, Nora, International Preliminary Report on Patentability, dated May 14, 2008 for International Application No. PCT/US2006/060879.
Noss, C.L. and V.P. Olivieri, "Disinfecting capabilities of oxychlorine compounds," Appl. Environ. Microbiol. 1985, vol. 50, pp. 1162-1164.
Office Action, dated Dec. 16, 2013, corresponding to counterpart Canadian Patent Application No. 2675574.
Rosenblatt et al., "The Reaction of Chlorine Dioxide with Triethylamine in Aqueous Solution," J. Org. Chem. (1963)28 10:2790-2794.
Singh, N. et al., "Efficacy of Chlorine Dioxide, Ozone, and Thyme Essential Oil or a Sequential Washing in Killing *Escherichia coli* O157:H7 on Lettuce and Baby Carrots," Lebesm.-Wissu.-Technol., 35, (2002) 720-729.
Canadian Search Report CA 2,629,888, dated Oct. 7, 2013.
White, G. C., "Handbook of Chlorination and Alternative Disinfectants," Wiley Interscience, 1999.
Written Opinion of the International Searching Authority dated Jul. 3, 2008 for International Application No. PCT/US2007/066081.
Young, "Humidity Control in the Laboratory Using Salt Solutions—Review", Appl. Chem. (1967) 17:241-245.
U.S. Office Action for U.S. Appl. No. 13/365,869, dated May 16, 2014.
U.S. Office Action for U.S. Appl. No. 13/365,885, dated Jun. 10, 2014.
U.S. Office Action for U.S. Appl. No. 13/365,902, dated Jun. 11, 2014.
U.S. Office Action for U.S. Appl. No. 13/365,912, dated May 16, 2014.
European Search Report EP 06 84 9144, dated Aug. 6, 2013.
U.S. Office Action for U.S. Appl. No. 13/365,902, dated Aug. 29, 2013.
U.S. Office Action for U.S. Appl. No. 13/365,885, dated Aug. 29, 2013.
EPA Guidance Manual on Alternative Disinfectants and Oxidant: Chlorine Dioxide, Apr. 1999, 4-1:4-41.
Water Boy 2011, retrieved online at http://www.waterboy.com/blog/distilled-and-purified-water/.
Canadian Office Action for CA 2,629,888, dated Sep. 11, 2014.
Canadian Office Action for CA 2,675,574 dated Oct. 6, 2014.
Chart of References (undated).
Notice of Allowance for U.S. Appl. No. 13/365,885, dated Dec. 31, 2014.
Notice of Allowance for U.S. Appl. No. 13/365,902, dated Dec. 24, 2014.
Decision of Appeal for U.S. Appl. No. 12/296,051 issued Jan. 15, 2015.
Notice of Allowance for U.S. Appl. No. 13/365,869, dated Nov. 10, 2014.
U.S. Office Action for U.S. Appl. No. 12/296,049, dated Sep. 26, 2014.
Non-Final Office Action for U.S. Appl. No. 12/196,051 dated Jan. 12, 2016.
Final Office Action for U.S. Appl. No. 12/296,051, dated May 3, 2016.
Canadian Office Action dated Feb. 26, 2016 for Canadian Application No. 2,629,888.
Canadian Examination Report dated Mar. 16, 2016 for Canadian Application No. 2,675,574.
Halox Technologies, Inc., Material Safety Data Sheet, Chlorine Dioxide Dissolved in Water, <0 . . . 54%(w/w), Jun. 21, 2014, http://haloxtech.com/pd/MSDS-Chlorinedioxide (Cl02)-540ppm.pfd.
European Examination Report for European Application No. 06849114.8, dated Aug. 19, 2016, 6 pages.
Canadian Office Action for Canadian Application No. 2,675,574 , dated Aug. 12, 2016—4 pages.
Entire Patent Prosecution History of U.S. Appl. No. 14/824,548, filed Aug. 12, 2015, entitled, Storage-Stable Aqueous Solutions of Chlorine Dioxide and Methods for Preparing and Using Them.
Canadian Office Action for Canadian Application No. 2,957,194, dated Jun. 1, 2018, 8 pages.
Canadian Office Action for Canadian Application No. 2,957,194, dated Apr. 15, 2019, 4 pages.
Canadian Office Action for Canadian Application No. 2,957,194, dated Feb. 4, 2020, 4 pages.
Canadian Examination Report for Canadian Application No. 2,957,194, dated Sep. 9, 2020, 4 pages.

STORAGE-STABLE AQUEOUS SOLUTIONS OF CHLORINE DIOXIDE AND METHODS FOR PREPARING AND USING THEM

RELATED APPLICATIONS

This application is a Continuation-in-Part of U.S. application Ser. No. 14/824,548, filed Aug. 12, 2015, which is a Continuation of U.S. application Ser. No. 12/296,049, filed Apr. 21, 2010, now U.S. Pat. No. 9,302,911, issued Apr. 5, 2016, which is a U.S. national phase filing of PCT Application No. PCT/US06/060879, filed Nov. 14, 2006, and claims priority of U.S. Provisional Application No. 60/736,636, filed Nov. 14, 2005, the entireties of which applications are incorporated herein by reference.

FIELD OF THE INVENTION

The present invention relates to storage-stable aqueous solutions of chlorine dioxide and methods for preparing and using storage-stable aqueous solutions of chlorine dioxide.

BACKGROUND

Chlorine dioxide is a strong, but highly selective oxidizer. It has been used in aqueous solution for many decades in various applications including disinfecting drinking water and in other water processing applications. One of its chief benefits is that it does not react with organic materials to form chlorinated hydrocarbons, which are increasingly avoided because of health concerns and regulatory pressure. In fact, chlorine dioxide can be used to destroy organic compounds that form chlorinated hydrocarbons, or to destroy chlorinated hydrocarbons after they have been formed.

Aqueous solutions of chlorine dioxide are also used in large quantities for bleaching paper pulp, where use of the chemical has greatly reduced the formation of chlorinated by-products compared to those formed by prior methods. Solutions of chlorine dioxide have been used extensively for decontamination of bio-contaminated buildings, enclosures, and articles. Chlorine dioxide solutions are also used extensively as a disinfecting wash for poultry, beef, and many types of fruits and vegetables.

Because of the instability of known chlorine dioxide solutions, these solutions are produced at the point of use and storage times are limited.

The Handbook of Chlorination and Alternative Disinfectants—4th Edition—George Clifford White, states that "aqueous solutions of chlorine dioxide are subject to photolytic decomposition, the extent of which is a function both of time and of the intensity of the ultraviolet component of the light source. Aqueous solutions of chlorine dioxide are known to retain their strength for longer periods of time if kept cool and properly stored in the dark." For many applications, however, refrigeration is expensive or impractical, and even with refrigeration the shelf life of chlorine dioxide produced in traditional ways is relatively short. For these reasons, most chlorine dioxide applications currently require generation of the chemical at, or near, the point of use. The literature abounds with references stating that unrefrigerated chlorine dioxide cannot be shipped or stored.

In the EPA Guidance Manual for Alternative Disinfectants and Oxidants (April 1999), the EPA instructs that chlorine dioxide must be made on-site.

U.S. Pat. No. 7,229,647 states that owing to its instability, chlorine dioxide has never been approved as a transportation chemical by the U.S. Department of Transportation of or the United Nations. U.S. Pat. No. 7,229,647 further states that on-site generation has been the only means for utilizing chlorine dioxide, which must be used within a day or two at most because 80-90% of its strength is typically lost within 24 hours. To aid in the decomposition of chlorine dioxide, U.S. Pat. No. 7,229,647 teaches the formation of a gel, which allows for 50% or higher of the initial chlorine dioxide concentration to remain after 90 days of storage.

U.S. Pat. No. 6,051,135 discloses an apparatus for producing chlorine dioxide and states that due to the inherent instability of aqueous chlorine dioxide solutions, the apparatus is intended to be used to manufacture chlorine dioxide on-site.

U.S. Pat. No. 7,666,384 states that aqueous solutions of chlorine dioxide rapidly degrade and as a result of the complex chemistry of chlorine dioxide and the often unwanted side reactions that occur, chlorine dioxide must be produced at the point of use.

U.S. Patent Application Publication No. 2002/0037248 teaches that the minimum decomposition rate of chlorine dioxide is 0.6% per hour, which occurs at a pH of 4.85 to 3.90.

The use of chlorine dioxide solutions has been limited because chlorine dioxide concentration must be kept low for safety reasons. Chlorine dioxide gas above such solutions can decompose spontaneously and exothermically if it reaches elevated concentrations. OSHA lists the safe limit as 10% (76 mm partial pressure) in air at atmospheric pressure. Other expert sources identify the limit as 16% (120 mm partial pressure) or even higher. At a partial pressure of 150 mm and higher, a spontaneous decomposition is quite mild and characterized as a "puff". At still higher concentrations, the decompositions become explosive, and at partial pressures of 225-300 mm or higher, explosions can be quite violent. The presence of water vapor elevates the concentration at which decompositions occur. FIG. 1 shows the vapor pressure of chlorine dioxide gas above aqueous solutions of the gas as a function of temperature and concentration. As with aqueous solutions of most gases, the solubility of chlorine dioxide decreases as temperature increases—i.e. for a given concentration of dissolved gas, the partial pressure of the gas above the solution at equilibrium is a positive function of temperature.

Several suppliers offer a liquid called "Stabilized Chlorine Dioxide", "Chlorine Dioxide Solution" or similar names. These materials are not chlorine dioxide, but dissolved sodium chlorite. When mixed with acid, they produce chlorine dioxide solutions, but this requires chemical mixing and handling of acid. Opportunities abound for errors in mixing and even when reagents are mixed properly the resulting solution may contain high levels of salt, acid, and other impurities. Moreover, after mixing, the chlorine dioxide solutions have a short shelf life.

Chlorine dioxide can be produced in a variety of ways. Most of the production processes suitable for use at less than a few thousand pounds per day are based on reaction of sodium chlorite with chlorine or acid in aqueous solution. Many of these processes are based on the reaction:

$$2NaClO_2 + Cl_2 \rightarrow 2ClO_2 + 2NaCl \qquad \text{(Reaction 1)}$$

All technologies where chlorine dioxide is produced in solution, whether produced from Reaction 1 or otherwise, produce chlorine dioxide solutions containing other products and by-products of the reaction plus unreacted feedstock reagents. Typical contaminants in these products include chlorine, various acids, sodium chlorite, sodium chlorate, and sodium chloride.

Impurities in aqueous chlorine dioxide solutions are also contributed from other sources, including the water used to prepare the chlorine dioxide solutions. Other sources of contamination include the containers used to prepare and store the aqueous chlorine dioxide solutions, as well as the apparatus used to produce the solutions.

The use of chlorine dioxide solutions has been limited because chlorine dioxide concentration must be kept low for safety reasons. Chlorine dioxide gas above such solutions can decompose spontaneously and exothermically if it reaches elevated concentrations. OSHA lists the safe limit as 10% (76 mm partial pressure) in air at atmospheric pressure. Other expert sources identify the limit as 16% (120 mm partial pressure) or even higher. At a partial pressure of 150 mm and higher, a spontaneous decomposition is quite mild and characterized as a "puff". At still higher concentrations, the decompositions become explosive, and at partial pressures of 225-300 mm or higher, explosions can be quite violent. The presence of water vapor elevates the concentration at which decompositions occur. FIG. 1 shows the vapor pressure of chlorine dioxide gas above aqueous solutions of the gas as a function of temperature and concentration. As with aqueous solutions of most gases, the solubility of chlorine dioxide decreases as temperature increases—i.e. for a given concentration of dissolved gas, the partial pressure of the gas above the solution at equilibrium is a positive function of temperature.

Even if the concentration of a solution is in a stable range, the shipment and storage of chlorine dioxide solutions must be done with care. It is commonly thought that chlorine dioxide cannot be shipped or stored. Thus, methods are needed for safely shipping and storing chlorine dioxide solutions.

For economic and logistical reasons, it is desirable to ship the most concentrated solutions that can safely be shipped. However, solutions packaged at low temperature under safe conditions might warm up and produce dangerous gas-phase concentrations. For example, solutions packaged at 5° C. and 15 g/L would have a headspace gas concentration of about 11 kPa (84 mm Hg partial pressure), which would be safe. If that same solution warmed up to 20° C., the headspace concentration would reach 20 kPa, which is near the region of spontaneous decomposition. If that solution warmed further to 60° C., the gas phase concentration could become quite dangerous. Solutions having a concentration below 3000 ppm by weight chlorine dioxide in water are regarded as safe for shipment in temperate climates. The gas in the head space above these liquids might reach 110-115 mm Hg if the temperature of the liquid reached 60° C. Solutions up to 2500 ppm could safely be allowed to reach 71° C., which is as high as temperatures are likely to reach in North America or Europe, even in unventilated enclosures in the sun. The use of ventilated warehouses and trucks, could permit still higher concentrations to be used. If the containers of solution could be reliably cooled, even without refrigeration, much higher concentrations are feasible. The extent to which water vapor elevates the safe concentration remains to be tested, but the fact that the gas in the head space of such containers will be saturated with water vapor provides an extra margin of safety.

Because chlorine dioxide is known as a strong, but highly selective oxidizer, it is highly desirable to use in water processing applications. However, the limits on the storage and transport of chlorine dioxide have greatly limited its use.

SUMMARY OF THE INVENTION

The present invention relates to stable aqueous chlorine dioxide solutions and methods of making and using stable aqueous chlorine dioxide solutions.

A first aspect of the present invention relates to a stable aqueous chlorine dioxide solution. The chlorine dioxide solution contains about 1000 ppm or less of total impurities. The solution may retain at least 75% of the original chlorine dioxide after 90 days at 25° C.

A second aspect of the present invention relates to a stable aqueous chlorine dioxide solution that contains about 1000 ppm or less of total impurities and/or 10 ppm or less of manganese and iron combined. The aqueous chlorine dioxide solution may retain at least 75% of the original chlorine dioxide after 90 days at 25° C.

A third aspect of the present invention relates to methods of making solutions of aqueous chlorine dioxide gas comprising contacting chlorine dioxide gas with water to prepare an aqueous solution of chlorine dioxide.

A fourth aspect of the present invention relates to methods for reducing the bacterial, viral or fungal load of an object comprising contacting an object carrying a bacterial, viral, or fungal load with an aqueous chlorine dioxide solution.

A fifth aspect of the present invention relates to delivering chlorine dioxide to a location in need of chlorine dioxide, comprising contacting chlorine dioxide gas with water to prepare an aqueous solution of chlorine dioxide, introducing the solution into a container, and transporting the container with the solution to the location in need of chlorine dioxide.

DETAILED DESCRIPTION

Figure 1:
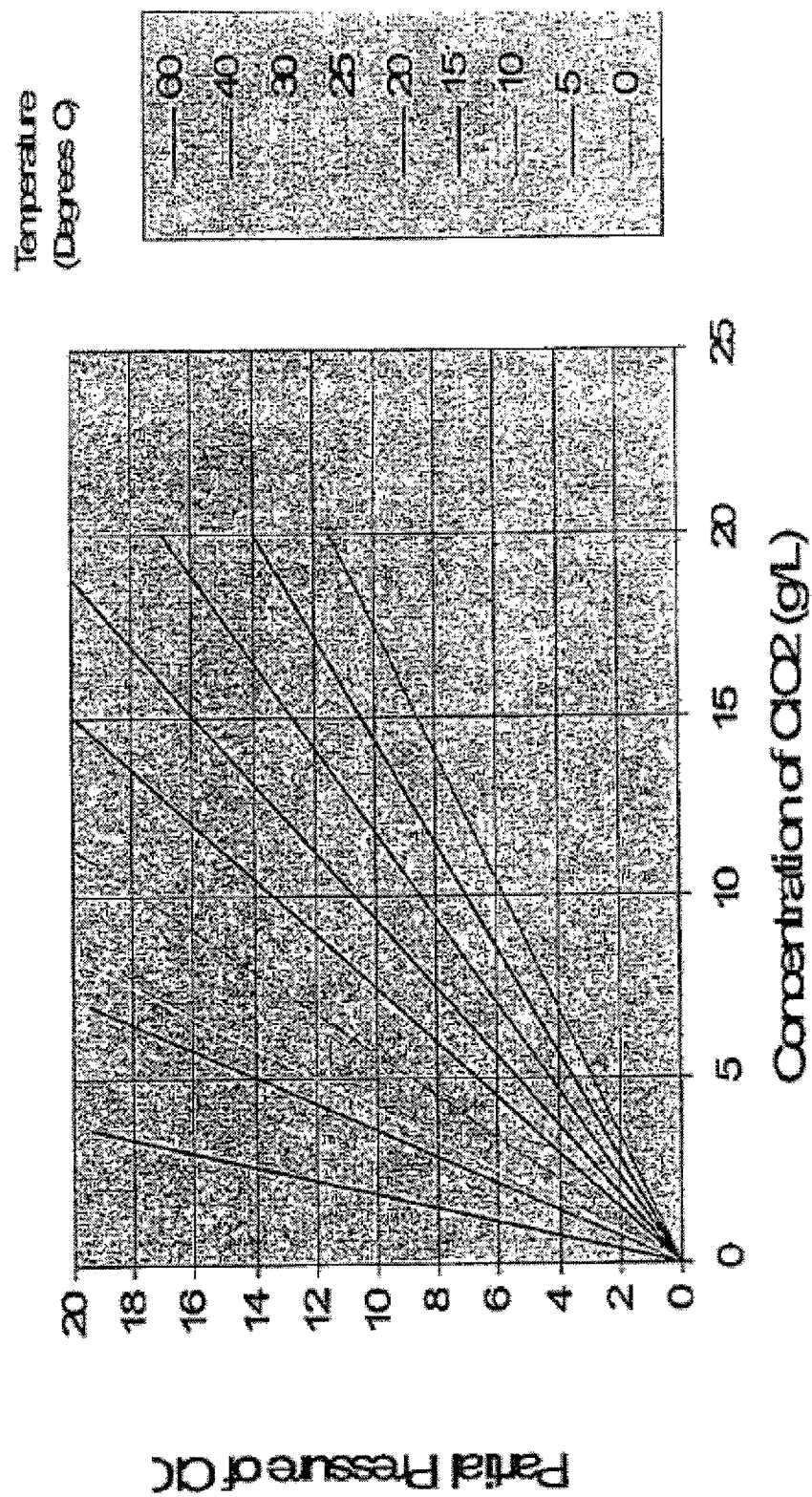
FIG. 1 provides a graphical representation of the dependence of $ClO_2$ partial pressure versus concentration in water as a function of temperature.

New storage-stable solutions of chlorine dioxide and methods for cleaning water for use in oil or gas production are disclosed herein.

As used herein, the term "stable" refers to the storage stability of an aqueous chlorine dioxide solution, i.e., its resistance to chemical degradation.

As used herein, the term "ready to use" means an aqueous chlorine dioxide solution that does not need to be produced for immediate use at the point of use. A ready to use aqueous chlorine dioxide solution may be produced at a remote location and transported to the point of use, such as an oil or gas well. For example, the ready to use aqueous chlorine dioxide solution can be stored for 90 days or more at a temperature of at least 25° C. and lose less than 25% of its initial chlorine dioxide concentration.

Unless stated otherwise, measurements in ppm refers to parts per million by weight.

The aqueous chlorine dioxide solutions according to the present disclosure can be prepared by contacting the pure water with ultra-pure chlorine dioxide. Any method for contacting the water with chlorine dioxide gas can be used so long as the gas dissolves in the water and the process does not introduce undesirable impurities into the solution. For example, this may be accomplished by bubbling the gas through the water. Alternatively, a counter-current packed column contactor can be employed such that water trickles down from the top of the column over packing while gas flows upward from the bottom of the column and chlorine dioxide solution drains from the bottom of the column.

Any suitable pure water can be used. Suitable water lacks substantial quantities of impurity that causes the shelf life of the aqueous chlorine dioxide to deteriorate below a desired shelf life. Suitable water can include deionized, distilled or water prepared by reverse osmosis or by a combination of these methods.

U.S. Pat. No. 5,234,678, incorporated herein by reference, discloses a simple and safe method for producing high purity chlorine dioxide gas. This process involves the reaction of a solid granular sodium chlorite with dilute chlorine gas according to Reaction 1. Unlike liquid phase production methods, the product resulting from this process does not contain significant quantities of sodium chlorite, sodium chlorate, or substantial quantities of sodium chloride, since these materials do not form gases to any appreciable extent. Tests by an independent lab have shown that the chlorine dioxide gas produced from this process can be over 99.95% pure. Systems for generating ultra-pure chlorine dioxide gas are available from CDG Environmental, LLC of Allentown, Pa.

Generally, the chlorine dioxide solutions of the invention are aqueous solutions containing about 2500 ppm or less of total impurities, more preferably 1000 ppm or less, more preferably about 500 ppm or less, even more preferably about 250 ppm or less and yet more preferably, about 100 ppm or less of total impurities.

The aqueous chlorine dioxide solutions preferably contain at least 100 ppm chlorine dioxide. According to at least one embodiment, the aqueous chlorine dioxide solutions contain at least 1000 ppm chlorine dioxide, at least 2000 ppm chlorine dioxide, at least 3000 ppm chlorine dioxide, at least 4000 ppm chlorine dioxide, at least 6000 ppm chlorine dioxide, at least 8000 ppm chlorine dioxide, at least 10,000 ppm chlorine dioxide, or more. It can be appreciated however, that the concentration of dissolved chlorine dioxide will depend on the temperatures the solution is likely to experience.

According to at least one embodiment, the aqueous chlorine dioxide solution contains 100 to 10,000 ppm chlorine dioxide, from 1000 to 8000 ppm chlorine dioxide, from 2000 to 8000 ppm chlorine dioxide, or from 3000 to 8000 ppm chlorine dioxide.

In an embodiment the solution can be prepared by contacting chlorine dioxide gas with water where the chlorine dioxide gas can have a concentration in the range of about 1 to about 15% by volume in a gas, such as an inert gas, nitrogen or air. Preferably, the water contains about 1000 ppm or, more preferably, about 500 ppm or less of contaminants by weight. The chlorine dioxide gas can be contacted with water by any suitable method that does not introduce contaminants or result in excessive loss. For example, the gas can be bubbled through the water, such as with a sparger. Alternatively, the solution can be prepared in a packed column with a flowing gas and flowing water such that the flowing gas flows up through the column as water trickles down over the packing in the column and the dissolved chlorine dioxide solution can be collected as the effluent from the bottom of the column. Such columns and packing can be obtained from Koch Glitsch, Inc. of Wichita Kans., for example.

In an embodiment the chlorine dioxide solutions can be stored at temperatures that may exceed at least 40° C., at least 25° C., or at least 20° C. In other embodiments, the chlorine dioxide solutions can be stored at temperatures below 40° C., below 25° C., below 20° C., below 15° C., below 10° C., and even below about 5° C. One of ordinary skill in the art will recognize that lower storage temperatures generally provide greater storage stability.

The aqueous chlorine dioxide solutions can be stored in containers that minimize loss of chlorine dioxide. Preferably the containers are flexible containers and have a head space over the stored chlorine dioxide solution of about 1 percent of the volume of the container or less.

Containers are also disclosed for holding chlorine dioxide solutions made of materials and with wall thickness such that the rate of chlorine dioxide loss from the container is reduced. In an embodiment, the container can be a glass bottle, ideally a bottle in which the glass is formulated to minimize transmission of ultraviolet light. In an embodiment the container can be made of a biaxially oriented polymer such as polyethylene terephthalate. In another embodiment, the container can be made from high density polyethylene (HDPE) such as is used in making plastic 55-gallon drums.

Provided that such chlorine dioxide solutions are stored in flexible containers with no head space, they can be safely shipped and stored at concentrations that would otherwise be unsafe because the partial pressure of gas above the solution would be less than 1 atmosphere over a very wide range of concentrations and temperatures. Since the pressure on the outside of the container will always be 1 atmosphere (adjusted for altitude), bubbles of concentrated chlorine dioxide cannot form inside the container. If the flexible container is not completely filled, then the container can withstand thermal expansion of the liquid and even mild exothermic decompositions in stray bubbles, if such were to occur.

Chlorine dioxide solutions can deteriorate by chemical degradation into chlorine, oxygen, chlorite, chlorate, or other decomposition products. Traditionally, it has been believed that this mechanism prevented long shelf life for chlorine dioxide solutions. The present invention is based in part on the surprising discovery that these decomposition reactions either do not occur or occur at very slow rates in solutions made of pure water and ultra-pure chlorine dioxide. Solutions made by reacting liquid reagents according to reaction 1 yield chlorine dioxide in addition to sodium chloride in an equimolar concentration, and possibly unreacted sodium chlorite and/or unreacted chlorine gas.

Figure 2:
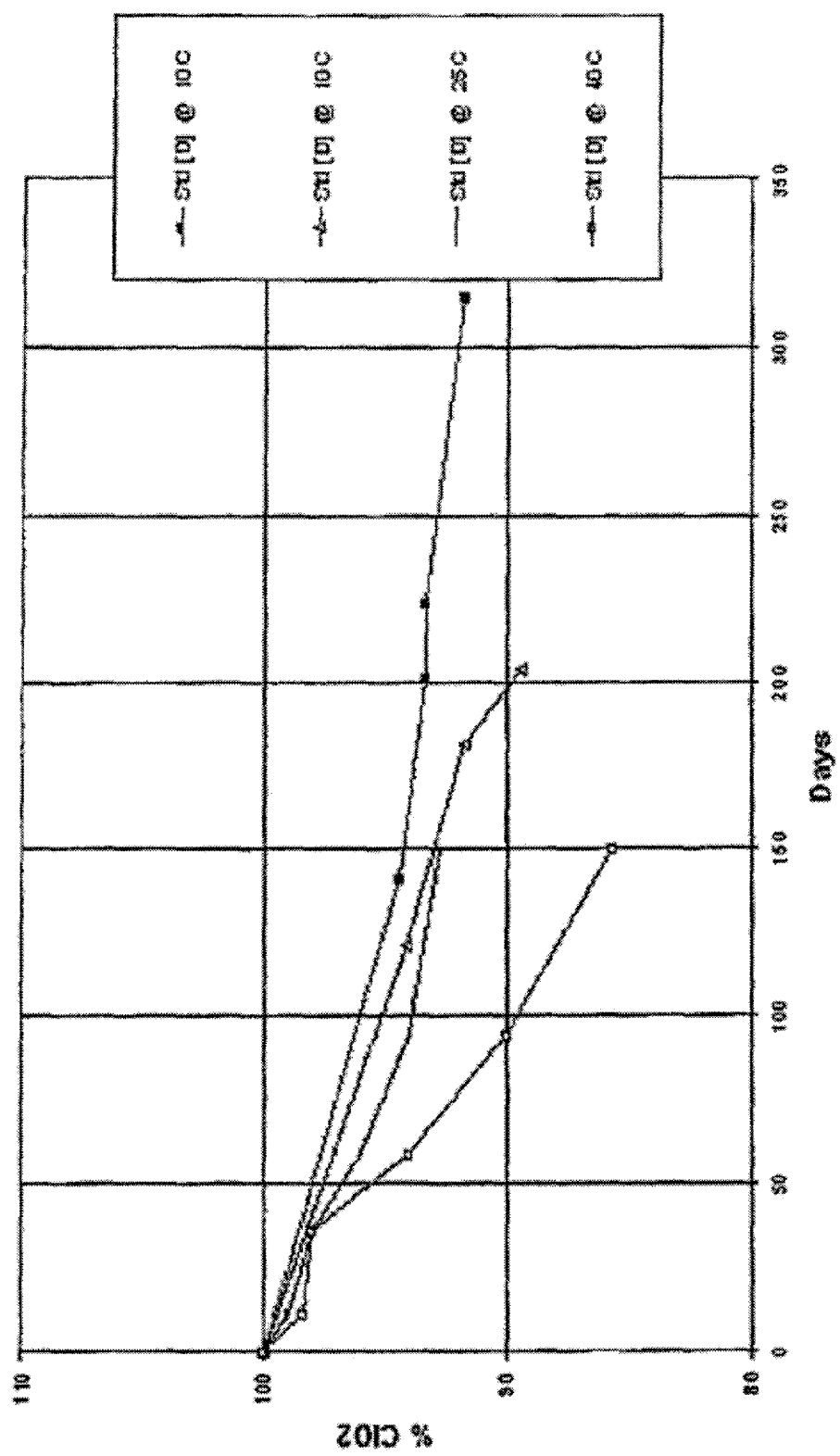
FIG. 2 provides a graphical representation of pure aqueous chlorine dioxide concentration when stored in amber glass bottles as a function of time and temperature with an initial chlorine dioxide concentration of about 4500 ppm.

FIG. 2 shows the stability of solutions of pure chlorine dioxide at about 3000 ppmw in pure water at various temperatures. Even at 40° C., the solution retains about 90% or more of its starting concentration for more than 90 days. This is considered commercially acceptable.

Figure 3:
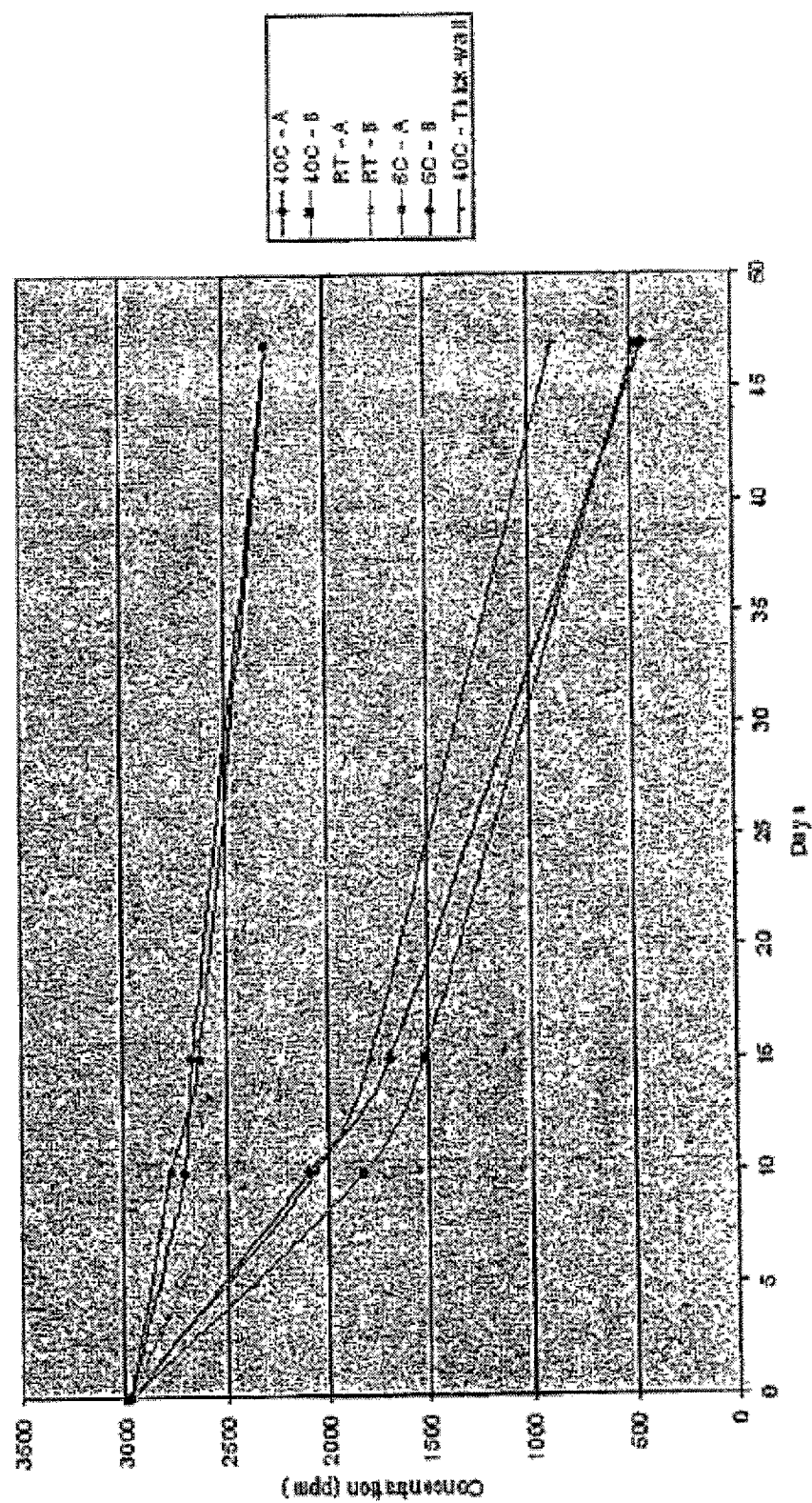
FIG. 3 provides a graphical illustration of the stability of aqueous chlorine dioxide solutions with 19% NaCl by weight at different temperatures in HDPE bottles.

Permeation of chlorine dioxide through the walls of a container occurs with many forms of container materials. Common plastics such as polyethylene, polypropylene and polycarbonate are known to be permeable to chlorine dioxide. If solutions are packaged in containers of these materials, the concentration of the chlorine dioxide will slowly decrease as it diffuses into and through the walls of the container. This process can be substantially eliminated by selection of the appropriate materials with an appropriate thickness. Testing of chlorine dioxide loss rates can be used to identify suitable materials for storage containers. FIG. 3 shows the chlorine dioxide concentration decrease as a function of time at various temperatures in 500 mL HDPE (high density polyethylene) bottles. In FIG. 3 "A" and "B" represent the results from separate but identical studies. This study demonstrated that the rate of loss of chlorine dioxide is a strong function of temperature. One of the curves in FIG. 3 is for a thick-walled HDPE bottle where the wall thickness is similar to that used in 55 gallon HDPE drums. This study further demonstrates that the loss rate of chlorine dioxide diffusion through the thick wall container is slower than through the thin walled container. This study also demonstrates that the rate of loss in the thick-wall bottle is initially equal to that in the thin. It is possible that this is because the rate of loss is initially determined by the rate at which gas diffuses into the inner surface of the bottle which is relatively fast. That rate would be the same for thick bottles as for thin. As time goes by, the wall becomes "saturated" and diffusion into the inner wall equals diffusion out of the outer wall. In this case, diffusion is slower through the thick wall. Because loss of concentration by permeation through the container walls is a function of surface to volume ratio of the container, the rate of concentration loss through the walls of an HDPE 55 gallon drum or larger HDPE container is negligible compared to the concentration decay due to other factors.

The effect of sodium chloride on the stability of chlorine dioxide solutions is very surprising. Although the shelf life of chlorine dioxide solutions can be affected by chemical "demand" in the water, sodium chloride would not theoretically exert any demand. It has been hypothesized that the presence of high levels of sodium chloride causes the reversal of Reaction 1 to re-form sodium chlorite and chlorine. Analysis of samples that have degraded because of the presence of sodium chloride shows the presence of significant quantities of chlorite ion, while none is detectable in the pure (unsalted) samples. However, the stoichiometry does not fully explain the amount of degradation apparent in FIG. 2. This demonstrates that additional factors are present that can lead to chlorine dioxide loss.

In many commercial applications, a shelf life of just a few days is adequate. For these applications small HDPE containers can be used for storage of aqueous chlorine dioxide. Desirably containers such as large 5 gallon or 55 gallon drums or even larger HDPE containers can be used to store chlorine dioxide solutions. Such containers, prior to use, can be pre-treated by filling with a pre-treatment solution containing chlorine dioxide or with dilute chlorine dioxide gas prior to filling with solution. This saturates the walls with chlorine dioxide and greatly slows initial chlorine dioxide losses. Shelf-life can be further extended by storing and shipping the filled containers under refrigeration and minimizing exposure to light or ultraviolet radiation.

Figure 4:
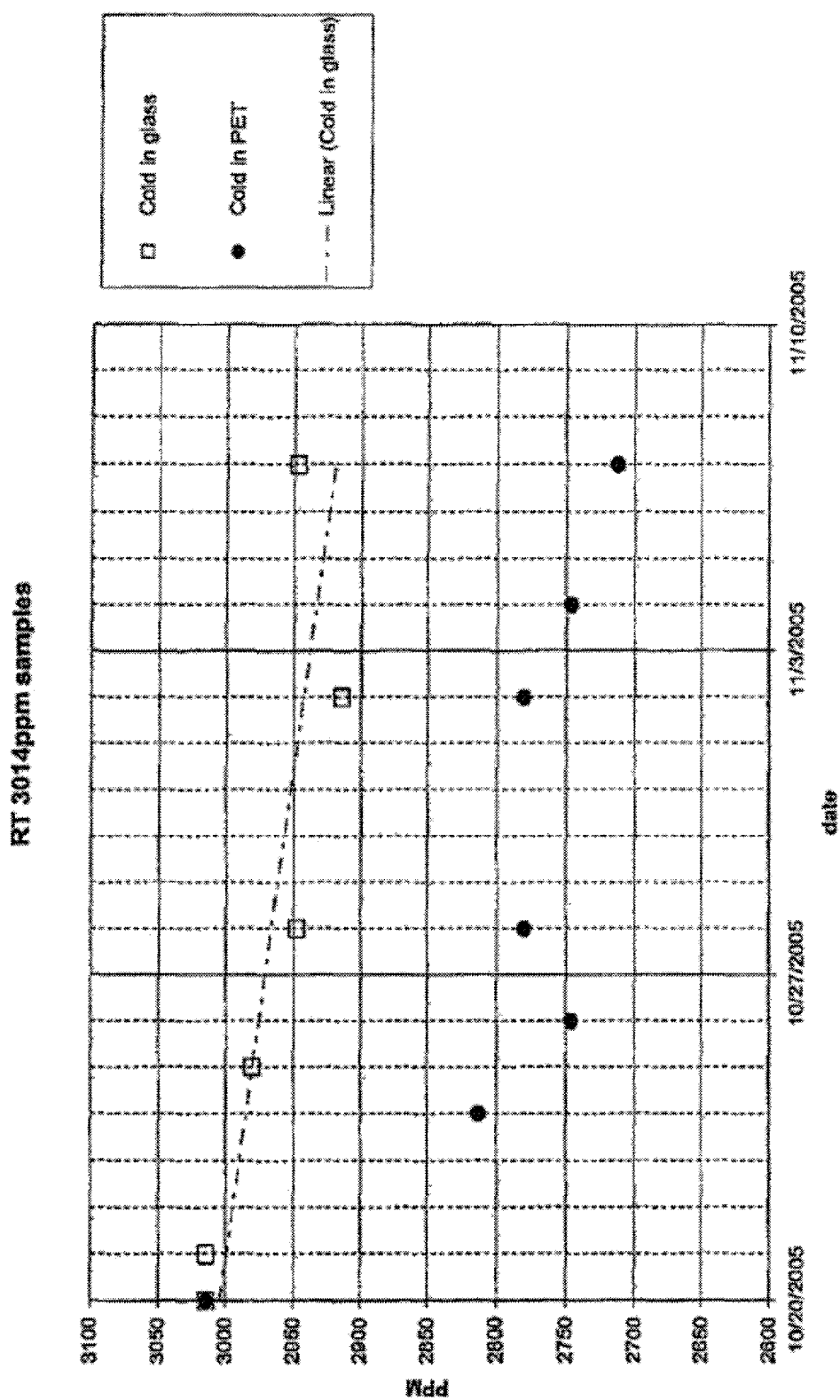
FIG. 4 provides a graphical illustration of the stability of chlorine dioxide solutions with 19% NaCl by weight and 4500 ppm chlorine dioxide in glass or PET bottles.

Other types of plastic containers exhibit superior barriers to permeation by chlorine dioxide from aqueous solutions. FIG. 4 shows the decay in concentration of solutions made with distilled water and stored in 750 mL bottles made of biaxially oriented PET (polyethylene terephthalate) polymer. After an initial rapid rate of loss, the solution in PET bottles is almost as stable as that stored in glass. Thus, after adjusting for the initial concentration loss, this study demonstrates that a solution of chlorine dioxide is storage stable in PET bottles.

The inventors have surprising discovered that certain contaminants have a significantly greater impact on the storage stability of aqueous chlorine dioxide solutions than others. To determine the impact of various contaminants, the inventors set up a series of experiments to test the effect of the contaminants at various concentrations. In each of the tests, the inventors prepared a chlorine dioxide gas that was more than 99% pure and greater than 99.97% chlorine-free with no detectable chlorine at the limits of detections. Because no other reagents or potential products are used to produce the chlorine dioxide gas, the product was determined to be substantially pure chlorine dioxide gas.

Pure water containing less than 1 ppm solid impurities was used to dissolve the chlorine dioxide gas and form the aqueous chlorine dioxide solutions at a concentration of 3000 ppm+/−5% chlorine dioxide as the initial starting concentration. The data in the figures is reported as % of starting concentration unless otherwise noted.

All data on concentration of aqueous solutions were measured by amperometric titration as described in EPA Standard Methods. Serial dilution was used to adjust to the range of the analytical device.

The accuracy of the analytical technique used is ±3%. Any variation of less than 3% is not considered significant. Apparent increases in concentration in a sealed container are attributable to measurement variability.

Loss of less than about 25% of starting concentration after about 90 days at elevated temperature is considered to represent commercially acceptable shelf life. This is significantly better than the reported shelf life of other common disinfectants such as sodium hypochlorite at comparable temperatures.

FIG. 2 shows the concentration of chlorine dioxide in distilled water in amber glass bottles as a function of time and temperature. FIG. 2 demonstrates surprising stability of aqueous chlorine dioxide solutions over the duration of the test. Further, the figure shows the temperature dependence of the chlorine dioxide loss within the range of 10° C. to about 40° C. In each case the solutions had a commercially acceptable shelf life. This data also shows that refrigerated solutions may have a shelf life of about a year or more. FIG. 2 includes data for chlorine dioxide solutions (4500 ppm chlorine dioxide starting concentration) in pure water with no added compounds.

Figure 5:
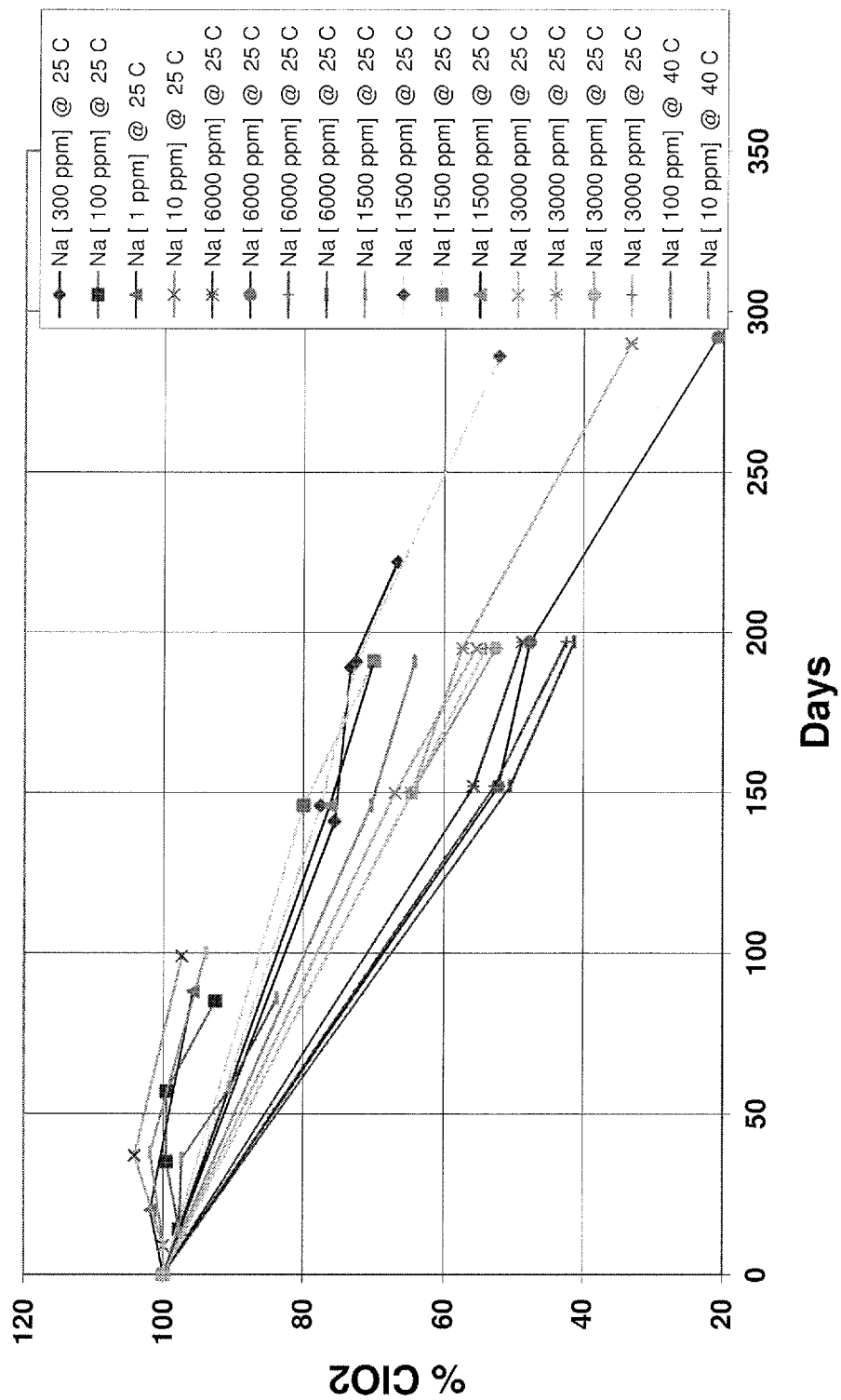
FIG. 5 provides a graphical representation of the stability of aqueous chlorine dioxide solutions having an initial chlorine dioxide concentration of 3000 ppm with sodium chloride at different concentrations and temperatures. 3000 ppm chlorine dioxide and 2600 ppm NaCl are approximately equimolar concentrations, such as would be produced in Reaction 1, if the reaction were carried out at perfect stoichiometric conditions.

FIG. 5 shows the concentration of pure chlorine dioxide in amber glass bottles as a function of time and temperature at different low levels of contamination with sodium chloride (NaCl). These studies show that, these chlorine dioxide solutions retain about 90% or more of their starting concentration for at least about 90 days except for the sample with 100 ppmw concentration of NaCl. These studies also demonstrate that salt substantially increases the rate of chlorine dioxide decomposition in solution and the resulting solutions do not retain the target concentration of 90% starting concentration for at least 90 days.

FIG. 5 also shows the effect of temperature and low levels of sodium chloride contamination on solutions of pure chlorine dioxide dissolved in otherwise pure water. Concentrations reported in the legend are concentrations of sodium ion. These samples were aged at 25 and 40° C. At 25° C. and up to 100 ppm NaCl, the samples were equally stable within the margin of error. At 100 ppm Na+ and 40° C. the chlorine dioxide deteriorated at a markedly higher rate.

Figure 6:
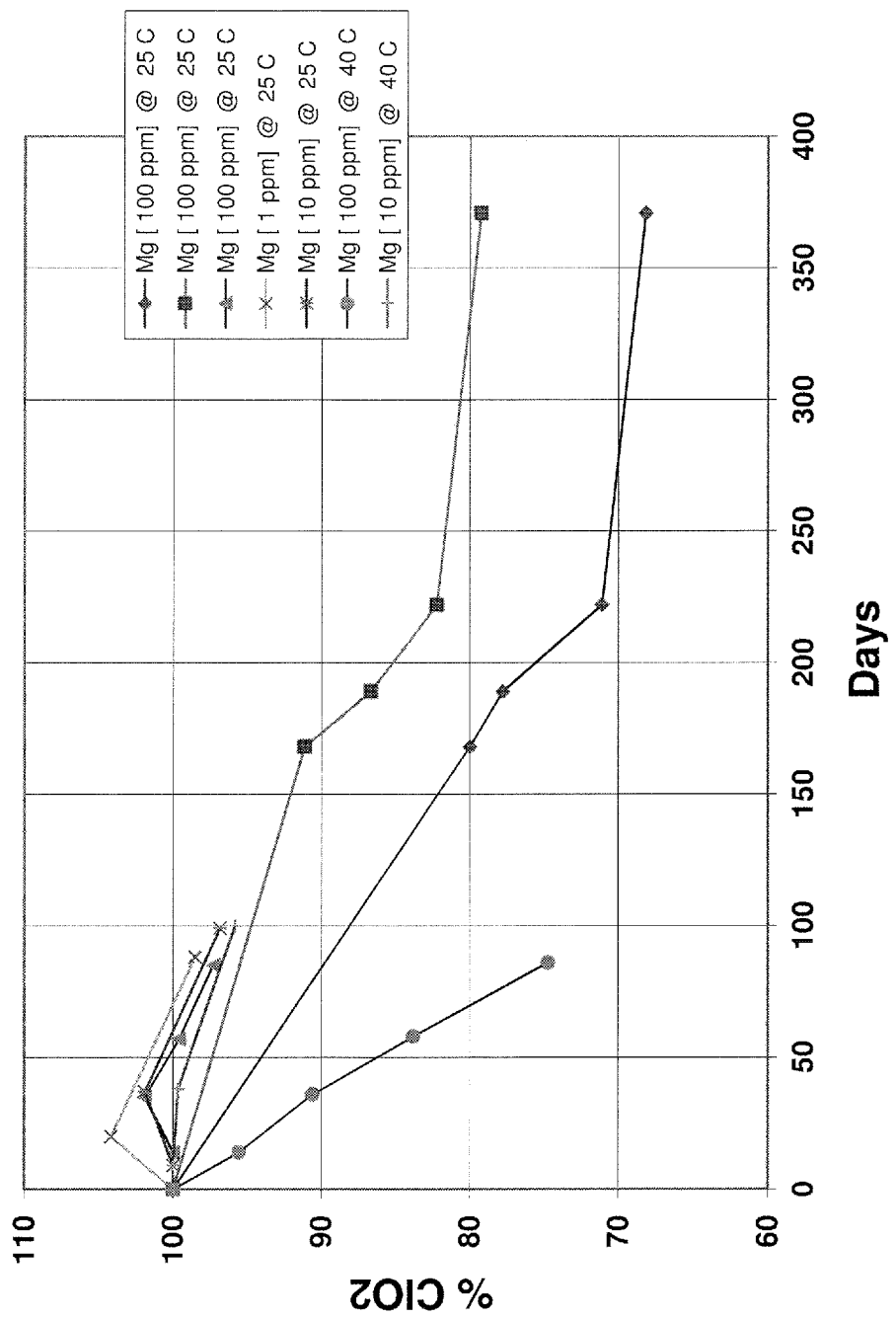
FIG. 6 provides a graphical illustration of the stability of aqueous chlorine dioxide solutions having an initial chlorine dioxide concentration of 3000 ppm and containing various concentrations of $MgCl_2$.
Figure 7:
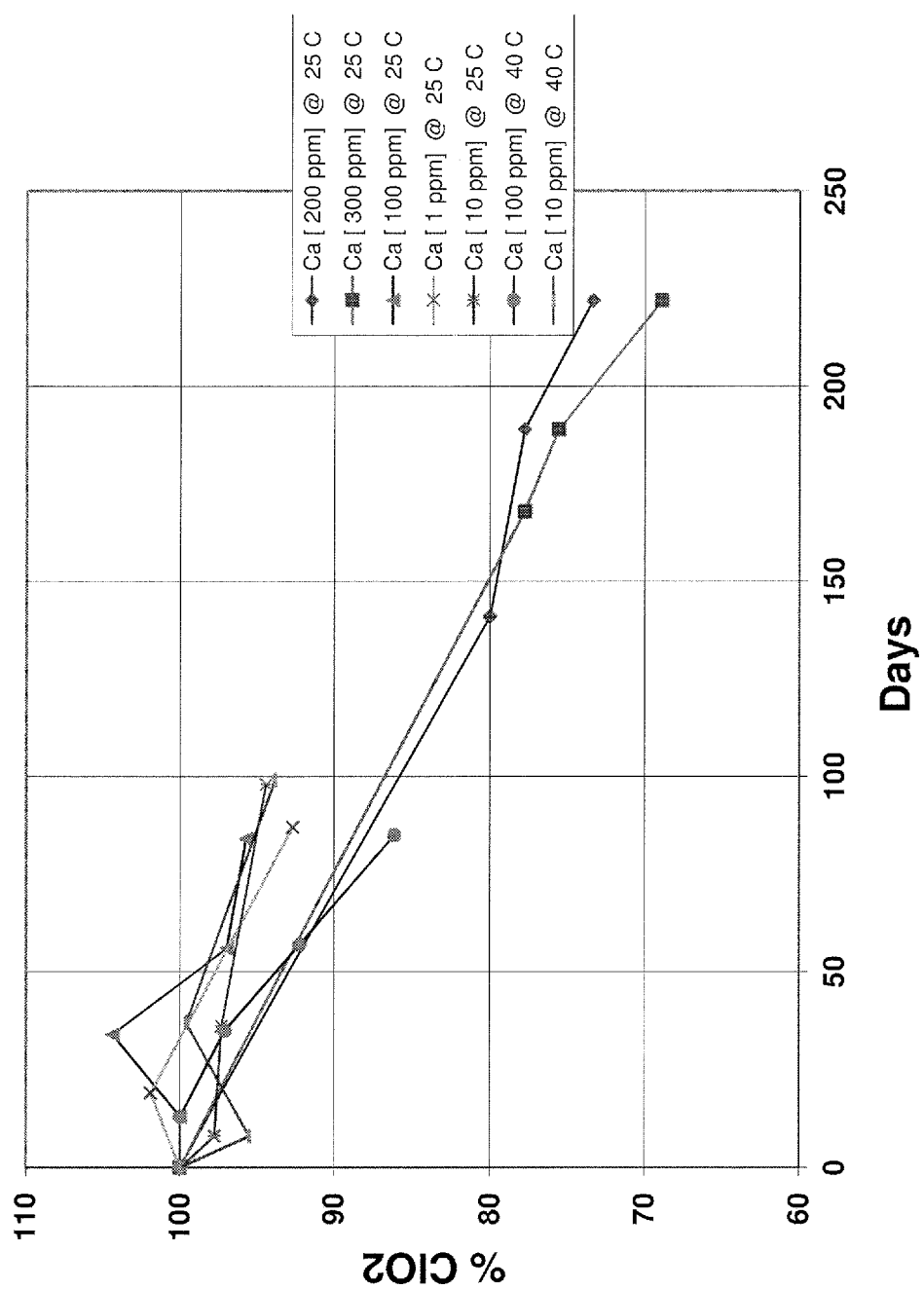
FIG. 7 provides a graphical illustration of the stability of aqueous chlorine dioxide solutions having an initial chlorine dioxide concentration of 3000 ppm and containing various concentrations of $CaCl_2$.
Figure 8:
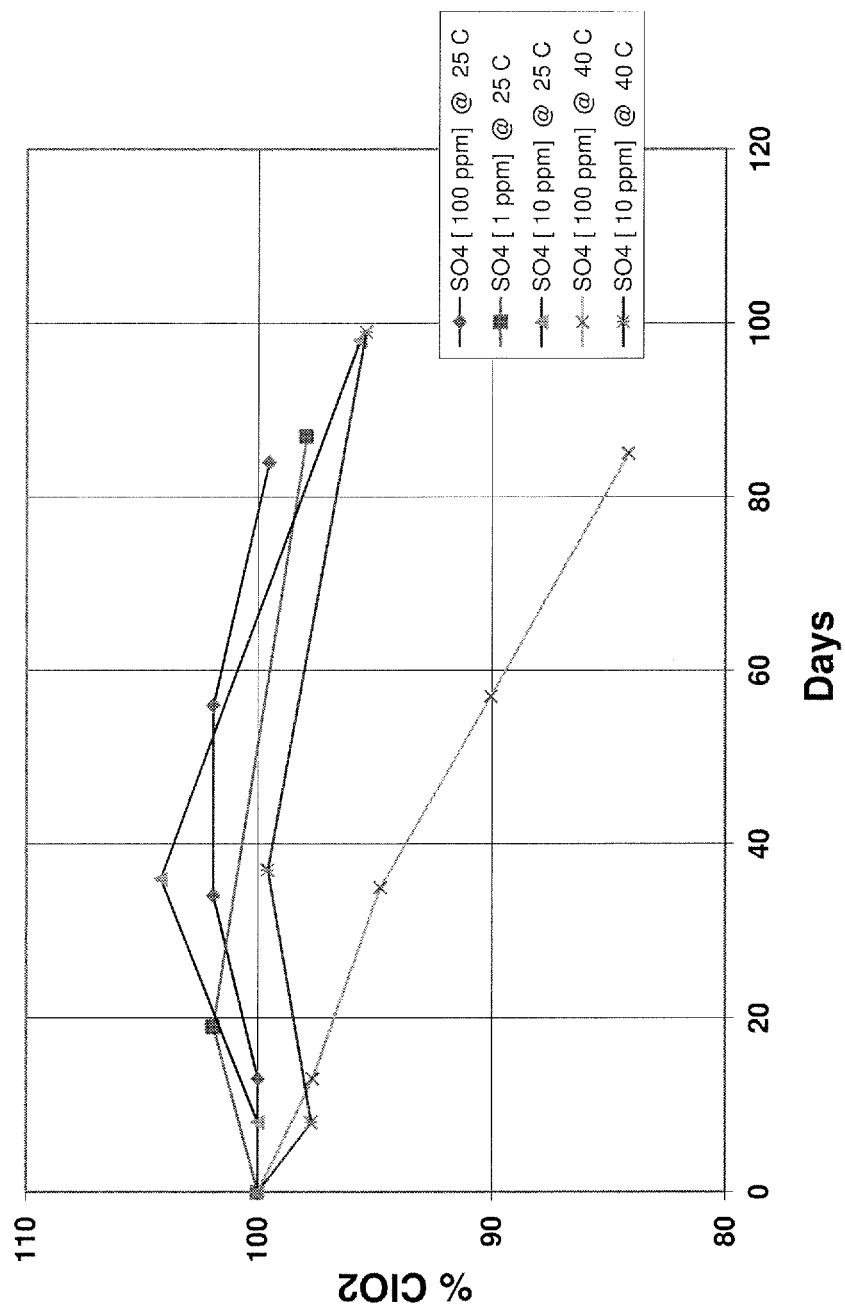
FIG. 8 provides a graphical illustration of the stability of aqueous chlorine dioxide solutions having an initial chlorine dioxide concentration of 3000 ppm and containing various concentrations of $Na_2SO_4$.
Figure 9:
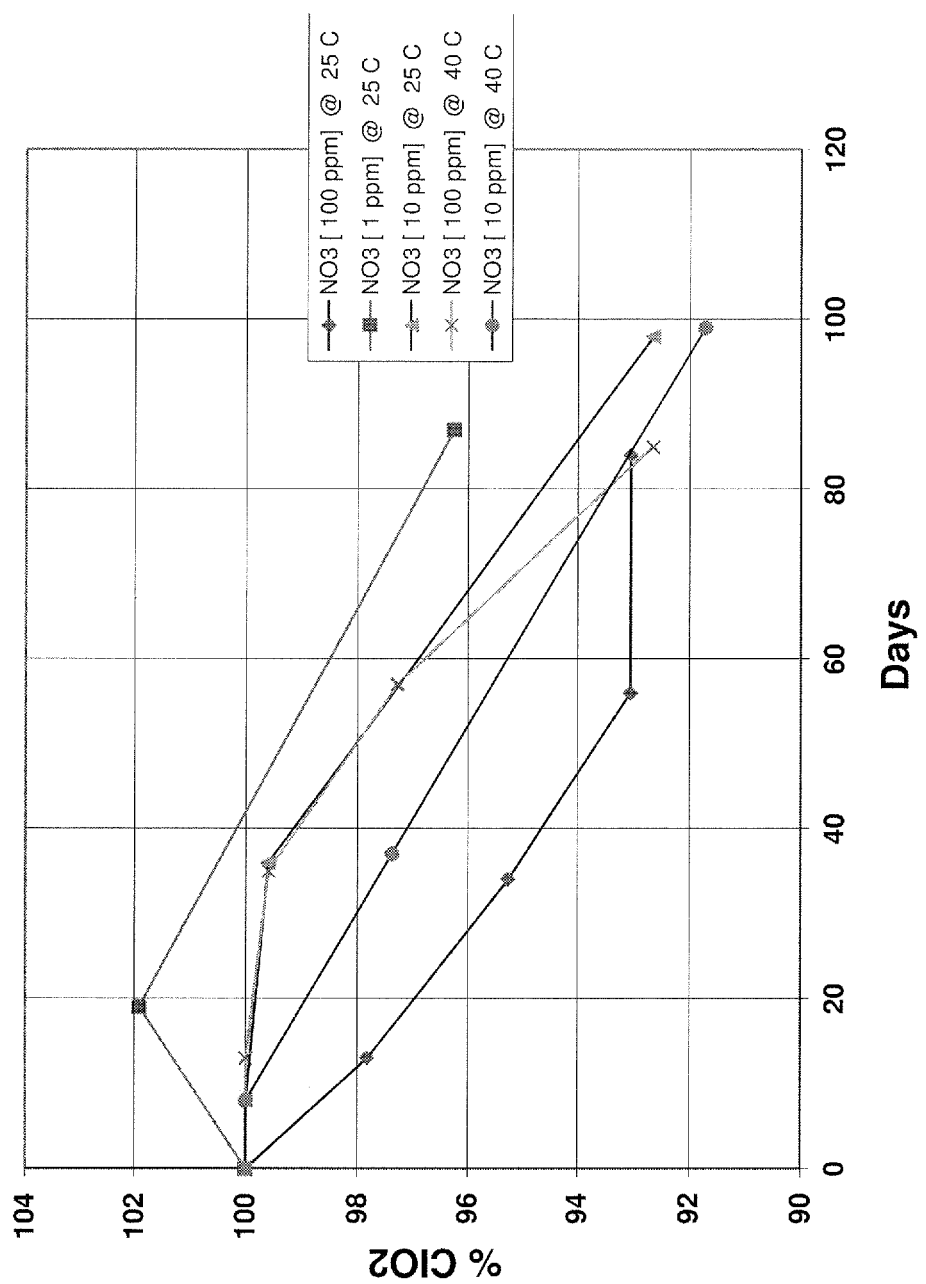
FIG. 9 provides a graphical illustration of the stability of aqueous chlorine dioxide solutions having an initial chlorine dioxide concentration of 3000 ppm and containing various concentrations of $NO_3$ ions.
Figure 11:
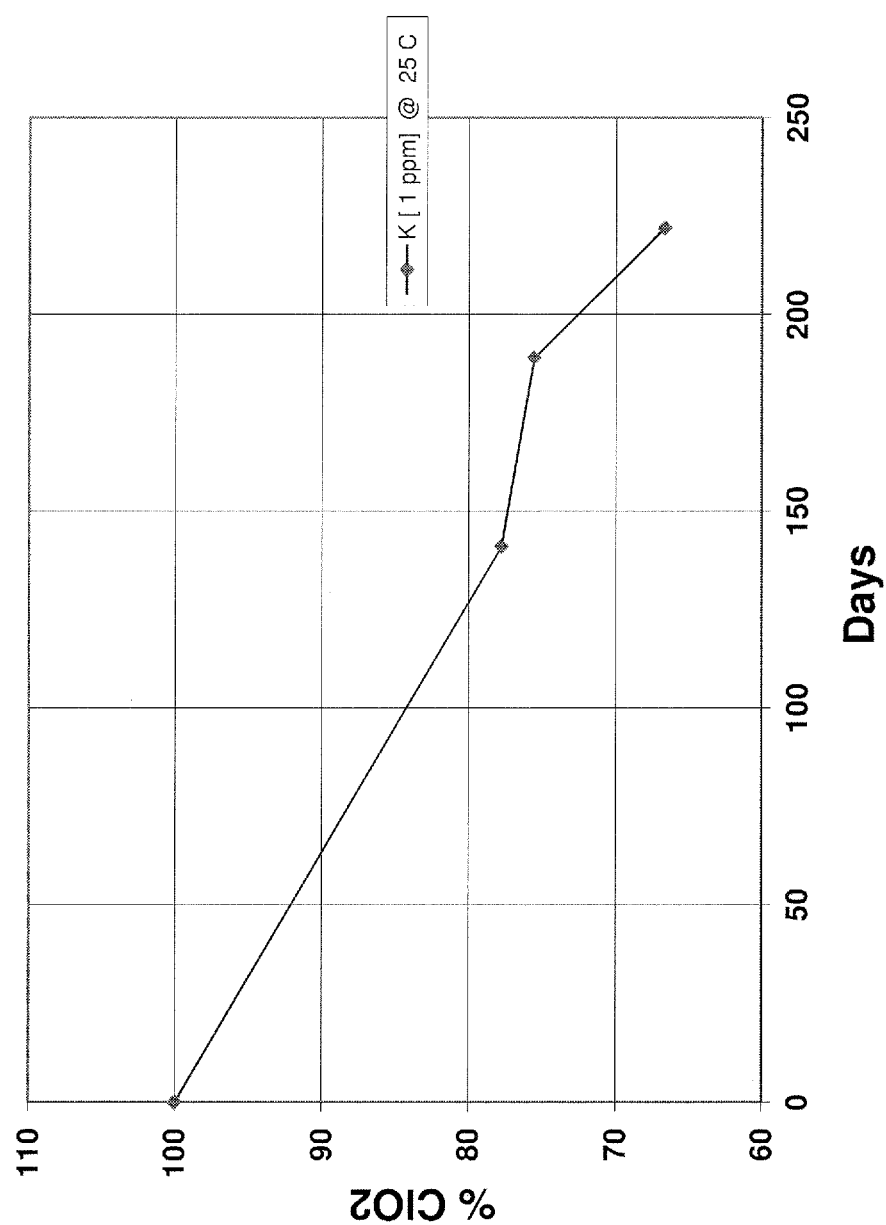
FIG. 11 provides a graphical illustration of the stability of aqueous chlorine dioxide solutions having an initial chlorine dioxide concentration of 3000 ppm and containing various concentrations of K ions.
Figure 12:
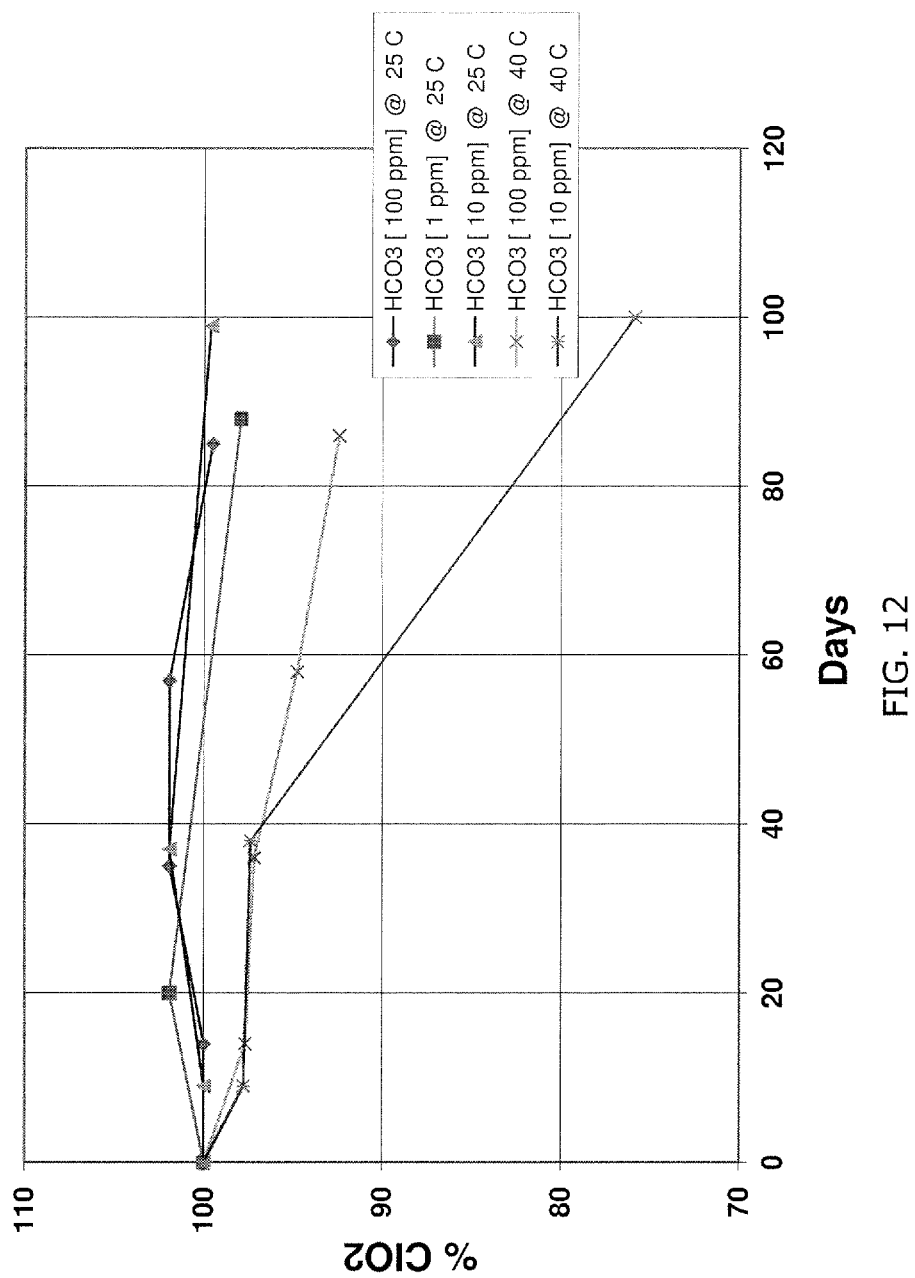
FIG. 12 provides a graphical illustration of the stability of aqueous chlorine dioxide solutions having an initial chlorine dioxide concentration of 3000 ppm and containing various concentrations of $HCO_3$ ions.
Figure 13:
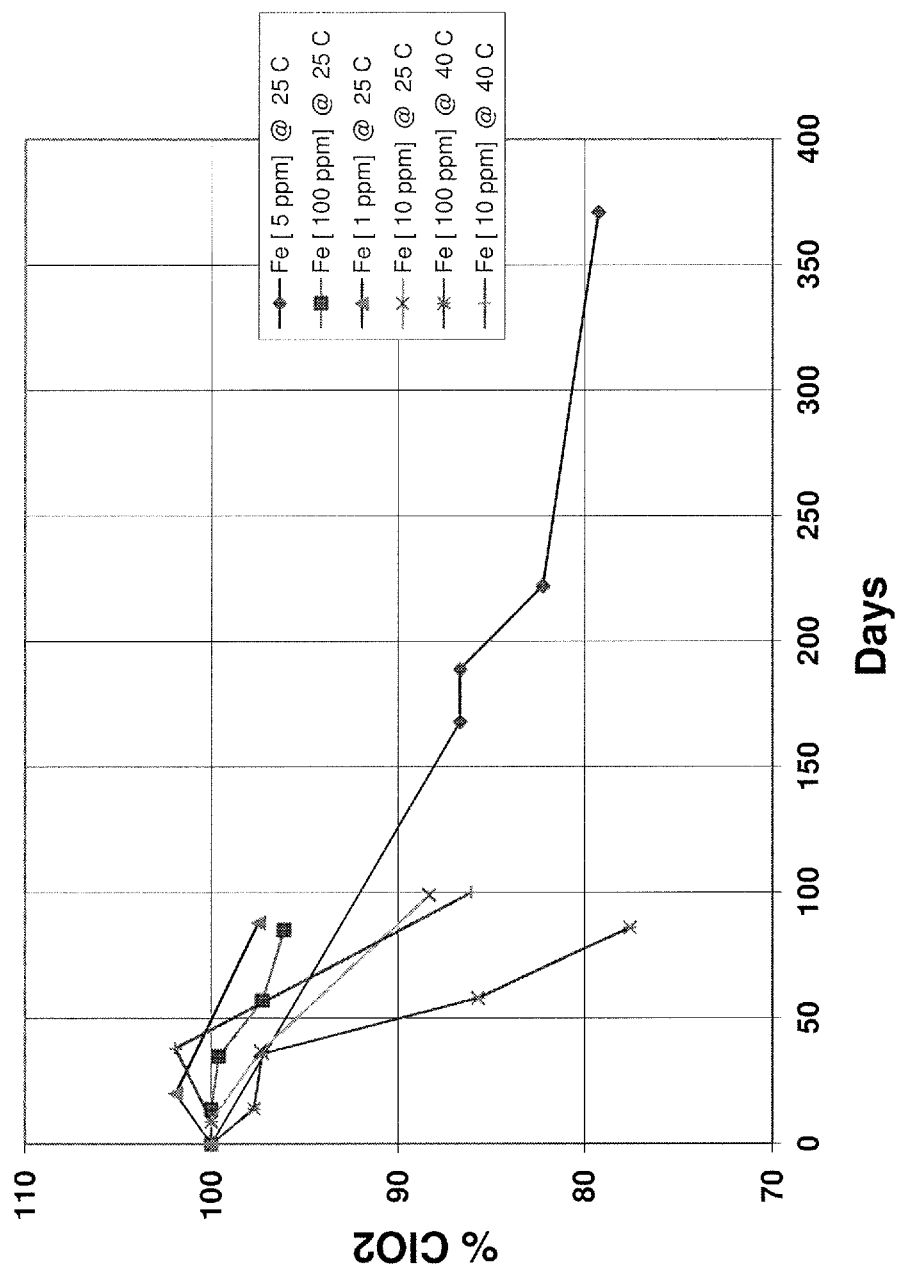
FIG. 13 provides a graphical illustration of the stability of aqueous chlorine dioxide solutions having an initial chlorine dioxide concentration of 3000 ppm and containing various concentrations of Fe ions.

Similar tests were performed using $MgCl_2$ (reported as concentration of Mg ion and shown in FIG. 6), $CaCl_2$ (reported as concentration of Ca ion and shown in FIG. 7), $Na_2SO_4$ (reported as concentration of $SO_4$ ion and shown in FIG. 8), nitrate ions (reported as concentration of $NO_3$ ions and shown in FIG. 9), manganese ions (reported as concentration of Mn ions and shown in FIG. 10), potassium ions (reported as concentration of K ions and shown in FIG. 11), bicarbonate ions (reported as concentration of $HCO_3$ ions and shown in FIG. 12), and iron ions (reported as concentration of Fe ions and shown in FIG. 13).

The data shows that increasing ion concentrations generally leads to greater chlorine dioxide decomposition (i.e., lower storage stability) over time.

This data indicates that 3000 ppm solutions of pure chlorine dioxide in water having less than 10 ppm contamination with alkali metal salts lose less than about 10% of their concentration in about 100 days at temperatures up to 40° C., while the same solutions having alkali metal salts at 100 ppm deteriorate at a much higher rate at 40° C. There is no statistically significant difference in the stability of the solutions at different temperatures and salt concentrations for temperatures of less than about 25° C. or concentrations of less than about 10 ppm. Only the combination of high temperature and high concentration accelerated decomposition. For much higher concentrations such as 1500-6000 ppm of salt, the loss of concentration was much higher than for salt concentrations of about 100 ppm or less, even at room temperature.

Chlorine dioxide solutions made by reacting sodium chlorite with chlorine in aqueous solution, which produces high concentrations of sodium chloride, are much less stable than solutions made using pure chlorine dioxide and pure water.

The data shown in FIGS. 5 to 13 shows that increasing contaminant concentrations leads to increased decomposition of the chlorine dioxide in the aqueous chlorine dioxide solutions.

According to at least one embodiment, the aqueous chlorine dioxide solution contains 100 ppm or less of metal impurities. In at least one embodiment, the aqueous chlorine dioxide solution contains 50 ppm or less of metal impurities, such as, for example, 25 ppm or less of metal impurities, or 10 ppm or less of metal impurities.

In at least one embodiment, the aqueous chlorine dioxide solution contains 100 ppm or less of transition metal impurities, such as, for example, 50 ppm or less of transition metal impurities, 25 ppm or less of transition metal impurities, or 10 ppm or less of transition metal impurities.

In at least one embodiment, the aqueous chlorine dioxide solution contains 100 ppm or less of alkali and alkaline metal impurities, such as, for example, 50 ppm or less of alkali and alkaline metal impurities, 25 ppm or less of alkali and alkaline metal impurities, or 10 ppm or less of alkali and alkaline metal impurities.

Figure 10:
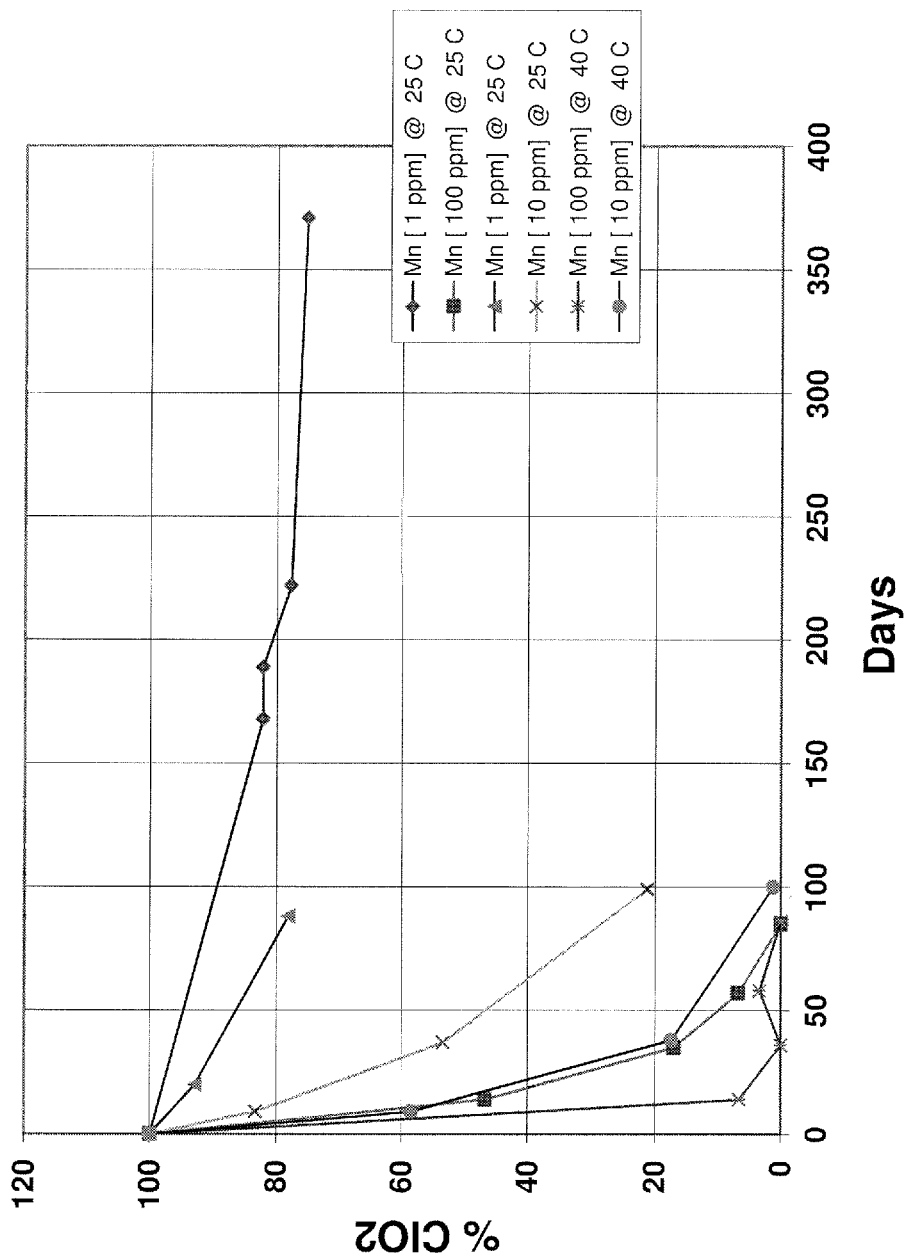
FIG. 10 provides a graphical illustration of the stability of aqueous chlorine dioxide solutions having an initial chlorine dioxide concentration of 3000 ppm and containing various concentrations of Mn ions.

The inventors have surprisingly discovered that the presence of manganese greatly affects the stability of aqueous chlorine dioxide solutions. As shown in FIG. 10, even small amounts of manganese ions (e.g., 10 ppm) can greatly diminish the storage stability of aqueous chlorine dioxide solutions. According to at least one embodiment, the aqueous chlorine dioxide solutions comprise 10 ppm or less of manganese, such as, for example, 5 ppm or less of manganese, or 1 ppm or less manganese.

According to at least one embodiment, the aqueous chlorine dioxide solution contain 100 ppm or less of iron, such as, for example, 10 ppm or less of iron, 5 ppm or less of iron, or 1 ppm or less of iron.

In at least one embodiment, the aqueous chlorine dioxide solution contains 10 ppm or less of iron and manganese impurities combined, such as 5 ppm or less iron and manganese impurities, or 1 ppm or less iron and manganese impurities.

According to at least one embodiment, the aqueous chlorine dioxide solutions contain 1000 ppm or less of total impurities and/or 10 ppm or less of manganese ions. In at least one further embodiment, the aqueous chlorine dioxide solutions contain 1000 ppm or less of total impurities and 1 ppm or less of manganese.

In at least one embodiment of the present invention, the aqueous chlorine dioxide solutions retain at least 75% of the original chlorine dioxide solution after 150 days at 25° C., such as at least 80% of the original chlorine dioxide solution or at least 90% of the original chlorine dioxide solution. In at least one embodiment of the present invention, the aqueous chlorine dioxide solutions retain at least 75% of the original chlorine dioxide solution after 90 days at 25° C., such as at least 80% of the original chlorine dioxide solution or at least 90% of the original chlorine dioxide solution According to at least one embodiment, the aqueous chlorine dioxide solutions retain at least 75% of the original chlorine dioxide solution after 90 days at 40° C., such as at least 80% of the original chlorine dioxide solution or at least 90% of the original chlorine dioxide solution.

The storage-stable solutions of chlorine dioxide disclosed herein can be used in any number of applications. For example the solutions can be diluted and used in topical treatments by contacting human skin, nails, wounds, and lesions with an amount of the solution. Diseases can be selected from the group of diseases caused by bacteria, viruses, and fungi. The solutions can be used in various water treatment applications by contacting water with an amount of the solution to reduce the amount of viable bacteria, viruses or fungi. Such water can include potable water, waste water, or recirculating water as is found in cooling towers or other recirculating water systems, as well as water used in oil production. The solutions can also be used to treat hard surfaces such as food preparation surfaces or surfaces in houses or buildings to reduce bacterial, viral or fungal loads.

Another aspect of the present invention relates to delivering chlorine dioxide to a location in need thereof. Aqueous chlorine dioxide solutions can be prepared as described above, such as, for example, by contacting chlorine dioxide gas with water to prepare an aqueous chlorine dioxide solution. The chlorine dioxide solution can be introduced into a container, such as those described above, and transported in the container to the location in need of chlorine dioxide. The chlorine dioxide may then be released from the solution for use, such as, by mixing the chlorine dioxide gas with a carrier gas and contacting an object to disinfect the object.

The examples and embodiments disclosed herein are provided for purposes of illustration only and are not intended to limit the scope of the claims of the invention.

We claim:

1. An aqueous chlorine dioxide solution containing about 1000 ppm by weight or less of total impurities, wherein the impurities are ions comprising:
   1,000 ppm by weight or less of sodium ions;
   200 ppm by weight or less of calcium ions;
   1 ppm by weight or less of manganese ions;
   100 ppm or less of magnesium ions;
   100 ppm or less of sulfate ions;
   100 ppm or less of nitrate ions;
   1 ppm or less of potassium ions;
   100 ppm or less of bicarbonate ions, and
   100 ppm or less of iron ions,
   wherein the concentration of chlorine dioxide in the solution is at least 1000 ppm by weight, and
   wherein the aqueous chlorine dioxide solution retains at least 75% of the original chlorine dioxide after 90 days at 25° C. when stored in an amber glass bottle.

2. The aqueous chlorine dioxide solution according to claim 1, wherein the aqueous chlorine dioxide solution contains 300 ppm by weight or less of sodium ions.

3. The aqueous chlorine dioxide solution according to claim 1, wherein the aqueous chlorine dioxide solution contains 100 ppm by weight or less of sodium ions.

4. The aqueous chlorine dioxide solution according to claim 1, wherein the aqueous chlorine dioxide solution contains 10 ppm by weight or less of magnesium ions.

5. The aqueous chlorine dioxide solution according to claim 1, wherein the aqueous chlorine dioxide solution contains 10 ppm by weight or less of sulfate ions.

6. The aqueous chlorine dioxide solution according to claim 1, wherein the aqueous chlorine dioxide solution contains 10 ppm by weight or less of nitrate ions.

7. The aqueous chlorine dioxide solution according to claim 1, wherein the concentration of chlorine dioxide in the aqueous chlorine dioxide solution is at least 2000 ppm by weight.

8. A method for reducing bacterial, viral or fungal load comprising contacting an object carrying a bacterial, viral or fungal load with the chlorine dioxide solution of claim 1.

9. The method according to claim 8, wherein the object is selected from the group consisting of a surface of an animal, water, a hard surface, and food.

10. The aqueous chlorine dioxide solution according to claim 1, wherein the concentration of chlorine dioxide in the aqueous chlorine dioxide solution is at least 4000 ppm by weight.

11. The aqueous chlorine dioxide solution according to claim 1, wherein the concentration of chlorine dioxide in the aqueous chlorine dioxide solution is at least 6000 ppm by weight.

12. The aqueous chlorine dioxide solution according to claim 1, wherein the aqueous chlorine dioxide solution contains 10 ppm by weight or less of bicarbonate ions.

13. The aqueous chlorine dioxide solution according to claim 1, wherein the aqueous chlorine dioxide solution contains 10 ppm by weight or less of iron ions.

14. The aqueous chlorine dioxide solution according to claim 1, wherein the aqueous chlorine dioxide solution contains about 500 ppm by weight or less of the total impurities.

15. The aqueous chlorine dioxide solution according to claim 1, wherein the aqueous chlorine dioxide solution contains about 250 ppm by weight or less of the total impurities.

* * * * *